(12) United States Patent
Henriksen et al.

(10) Patent No.: US 6,355,461 B2
(45) Date of Patent: *Mar. 12, 2002

(54) NON-AQUEOUS, LIQUID, ENZYME-CONTAINING COMPOSITIONS

(75) Inventors: Lotte Rugholm Henriksen, Vanløse; Mads Lykke, Brønshøj, both of (DK)

(73) Assignee: Novozymes A/S, Bagsvaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/174,202

(22) Filed: Oct. 16, 1998

Related U.S. Application Data

(63) Continuation of application No. PCT/DK97/00194, filed on Apr. 29, 1997.

(30) Foreign Application Priority Data

Apr. 29, 1996 (DK) .............................. 0513/96
Sep. 16, 1996 (DK) .............................. 0996/96

(51) Int. Cl.⁷ .............................. C12N 9/02; C12P 3/00
(52) U.S. Cl. ...................................... 435/189; 435/267
(58) Field of Search .................................. 435/189, 267

(56) References Cited

U.S. PATENT DOCUMENTS

| | | | |
|---|---|---|---|
| 4,370,199 A | * 1/1983 | Orndorff | 162/161 |
| 4,943,530 A | 7/1990 | Christner et al. | 435/188 |
| 5,389,369 A | * 2/1995 | Allen | 424/94.4 |
| 5,453,284 A | * 9/1995 | Pellico | 424/94.4 |
| 5,693,516 A | * 12/1997 | Blinkovsky | 435/188 |
| 5,700,770 A | * 12/1997 | Damhus et al. | 510/305 |
| 5,795,855 A | * 8/1998 | Schneider et al. | 510/376 |
| 5,866,393 A | * 2/1999 | Fuglsang et al. | 435/192 |
| 5,912,405 A | * 6/1999 | Schneider et al. | 8/111 |

FOREIGN PATENT DOCUMENTS

| | | |
|---|---|---|
| WO | WO 94/12620 | 6/1994 |
| WO | WO 94/12621 | 6/1994 |
| WO | 95/27046 | * 10/1995 |
| WO | 96/10079 | * 4/1996 |
| WO | WO 96/12845 | 5/1996 |
| WO | WO 96/12846 | 5/1996 |
| WO | 97/41215 | * 11/1997 |
| WO | 99/23887 | * 5/1999 |

OTHER PUBLICATIONS

Lugaro et al., Arch. Biochem. Biophys., 159(), "The Oxidation of Steroid Hormones by Fungal Laccase in an Emulsion of Water and Organic Solvents", pp. 1–6, Nov. 1973.*
Kilbanov, A. M., Chemtech, vol. 16, "Enzymes That Work in Organic Solvents", pp. 354–359, Jun. 1986.*
Doddema, H.J., Biotechnol. Bioengineer., 32(5), "Site–Specific Hydroxylation of Aromatic Compounds by Polyphenol Oxidase in Organic Solvents and in Water", pp. 716–718, Aug. 1988.*
Zaks et al., J. Biol. Chem., 263(17), "The Effect of Water on Enzyme Action in Organic Media", pp. 8017–8021, Jun. 1988.*
Milstein et al., Appl. Microbiol. Biotechnol., 31(1), "Oxidation of Aromatic Compounds in Organic Solvents with Laccase from Trametes versicolor", pp. 70–74, Jul. 1989.*
van Earp et al., Eur. J. Biochem. 202(2), "The Effect of Water Content and Nature of Organic Solvent on Enzyme Activity in Low–Water Media", pp. 379–384, Dec. 1991.*
Milstein et al., J. Biotechnol., vol. 30, "Transformation of Lignin–Related Compounds with Laccase in Organic Solvents", pp. 34–47, 1993.*
Monot, F., Ruvue de L'Institut Francais du Petrole, 49(2), "Enzymatic Catalysis in Organic Media", pp. 187–208, Apr. 1994.*
Rogalski et al., J. Molec. Catal., 95(1), "Immobilization of Laccase from Phlebia radiata on Controlled Porosity Glass", pp. 99–108, Jan. 1995.*
Dahiya et al., J. Basic Microbiol., 38(5–6), "Characterization of Laccase Produced by Coniothyrium minitans", pp. 349–359, Jul. 1998.*
Burdick & Jackson Laboratories, Inc., "High Purity Solvents Guide", various pp, 1982.*

* cited by examiner

Primary Examiner—Jon P. Weber
(74) Attorney, Agent, or Firm—Elias M. Lambris; Jason I. Garbell

(57) ABSTRACT

A substantially water-free, liquid, enzyme-containing composition comprises: (A) an enzyme; (B) a substance selected from (i) substances which in aqueous medium are substrates for said enzyme, (ii) substances which in aqueous medium are precursors for substrates for said enzyme, and (iii) substances which are cofactors for said enzyme; and (C) a non-aqueous liquid phase.

5 Claims, 1 Drawing Sheet

NON-AQUEOUS, LIQUID, ENZYME-CONTAINING COMPOSITIONS

CROSS-REFERENCE TO RELATED APPLICATIONS

Figure 1:
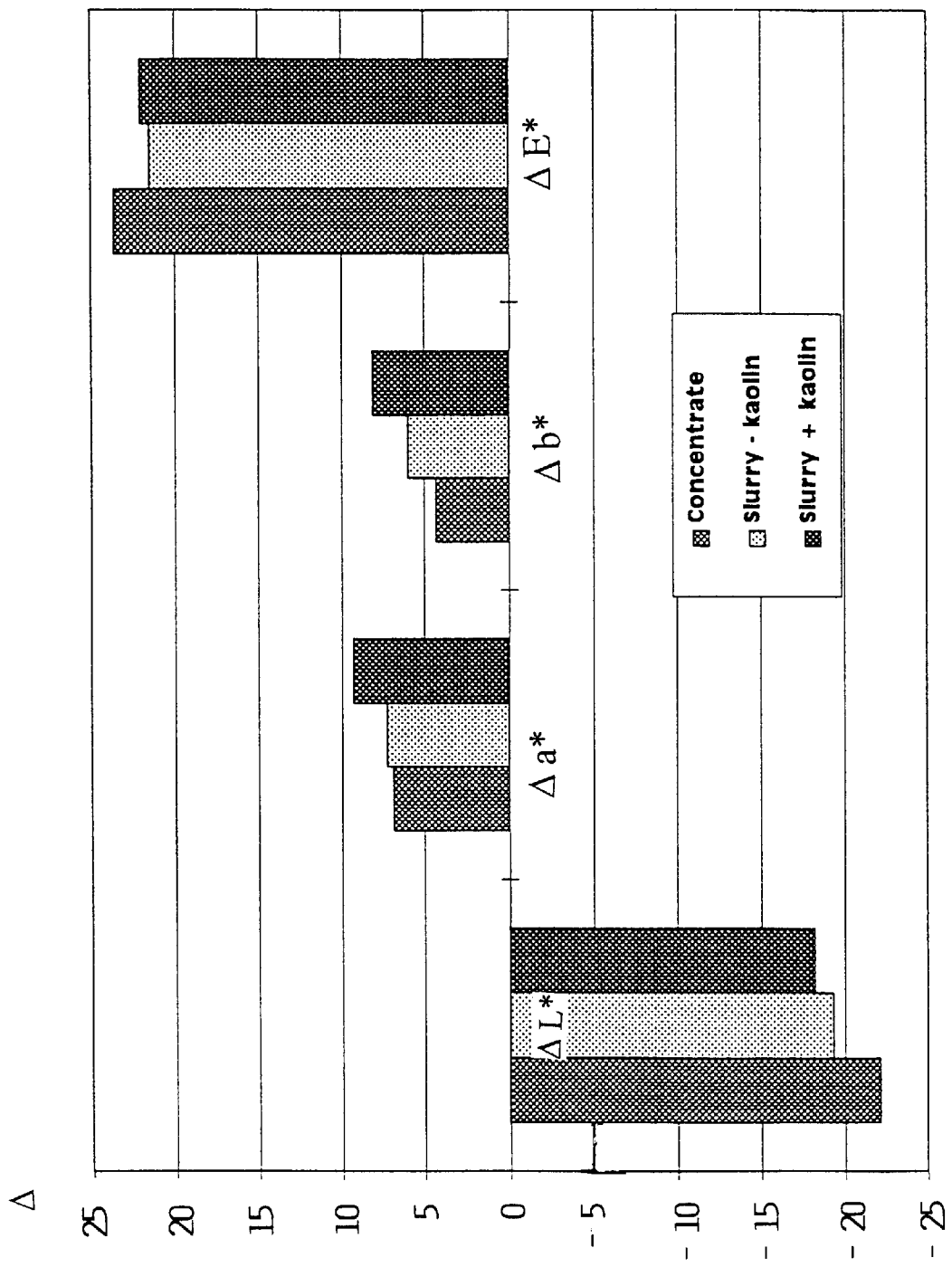

This application is a contination application of Ser. No. PCT/DK97/00194, filed on Apr. 29, 1997, and claims priority under 35 U.S.C. 119 of Danish application 0996/96, filed Sep. 16, 1996 and application No. 0513/96, filed Apr. 29, 1996, the contents of which are fully incorporated herein by reference.

FIELD OF THE INVENTION

The present invention relates to substantially anhydrous (i.e. substantially water-free) liquid compositions comprising: 1) an enzyme; 2) a substance which (a) in aqueous medium is a substrate for the enzyme, (b) in aqueous medium is a precursor for a substrate for the enzyme, or (c) is a cofactor for the enzyme; and 3) a non-aqueous liquid phase.

The invention is well suited to a wide variety of both non-food and food applications.

BACKGROUND OF THE INVENTION

Industrial enzymes have generally been formulated as particulate solids (e.g. in powder or granulated form, optionally with a coating of some kind) or in the form of a water-based solution. A number of solid formulations (e.g. enzyme powders) have the disadvantage that dust formation readily takes place, which—unless special precautions are taken—may result in contamination of the surrounding environment and thereby pose a risk to the health of persons handling such formulations.

While the use of water-based, liquid enzyme formulations essentially eliminates risk of dust formation, owing to the fact that practically all enzymes exert their activity in the presence of water it is generally not feasible to prepare storage-stable formulations of this type which incorporate— in one and the same composition—a free (e.g. unencapsulated or uncoated) enzyme and, for example, a substance which is a substrate for the enzyme (including in this connection an enzyme substrate which, via the agency of the enzyme, and normally in combination with one or more further reactants or reagents, reacts to form a species which undergoes a further subsequent reaction of importance in connection with the particular purpose for which the liquid enzyme formulation is intended).

By way of example, in connection with the use of a peroxidase in conjunction with an oxidizable substance known as a "mediator" (also known as an "enhancer" or an "accelerator")—e.g. a mediator of the substituted phenothiazine or substituted phenoxazine type—for the purpose of "dye-transfer inhibition" (i.e. inhibition of fabric-to-fabric transfer of dye) in connection with washing of dyed fabric or textiles (see, e.g., WO 94/12621), or for bleaching fabrics, e.g. denim fabrics (as described in WO 96/12845 and WO 96/12846), it will generally not be possible to include the peroxidase and the mediator (and, optionally, a source of hydrogen peroxide) in one and the same, water-based, liquid composition without rapid oxidation, and subsequent transformation, of the mediator taking place.

With reference again, by way of example, to the above-mentioned bleaching of fabric (such as denim fabric), when employing currently available liquid enzyme formulations the relatively short time span within which it is possible to operate once the enzyme (e.g. a peroxidase) has been brought into contact with the mediator will often necessitate (i) the establishment of separate containers or vessels (tanks or the like) each containing one of the interacting components, and from which the individual components can be dosed to the medium (aqueous medium) in which the bleaching process is to take place, and (ii) dosing of the individual components from the respective containers to the medium in the correct amounts and correct relative proportions. Thus, not only are multiple containers required, but it is also necessary to perform multiple unit operations (including multiple dispensing and dosing operations).

There is thus a need for liquid, storage-stable compositions which (a) contain not only an enzyme, but also a substance (e.g. a substance of one of the types mentioned earlier, above) which otherwise—in the presence of water and via the agency of the enzyme—will undergo a reaction of interest, and (b) are suited for subsequent introduction into or contact with an aqueous medium, thereby initiating the reaction in question. The present invention provides compositions fulfilling this need.

DETAILED DESCRIPTION OF THE INVENTION

The present invention thus relates to a substantially water-free liquid composition comprising:

(A) an enzyme;

(B) a substance (i.e. one or more substances) selected from (i) substances which in aqueous medium are substrates for said enzyme, (ii) substances which in aqueous medium are precursors for substrates for said enzyme, and (iii) substances which are cofactors for said enzyme; and (C) a non-aqueous liquid phase.

The term "substantially water-free" as employed in the present specification and claims in connection with a liquid composition of the invention is intended to indicate that the water content of the composition [normally to be understood as the content of free (unbound) water in the composition] is sufficiently low to ensure a thermodynamic activity of water in the composition which is low enough to hinder the onset of interaction between, on the one hand, the enzyme(s) in question and, on the other hand, the substrate(s), substrate precursor(s) and/or cofactor(s) in question.

The acceptable upper limit for the water content of a given type of embodiment of a composition according to the invention will depend, inter alia, on the nature of the enzyme, the nature and properties of the enzyme substrate, enzyme substrate precursor or enzyme cofactor, and the nature and properties of the non-aqueous liquid phase. For some types of embodiments of compositions of the invention, it may be possible to prepare satisfactorily stable compositions having a water content of about 5% w/w, or possibly even higher. However, a water content not exceeding about 2% w/w is normally to be preferred.

For numerous embodiments of compositions of the invention (e.g. compositions of the types exemplified and tested in the working examples herein), a more preferable upper limit for water content will normally be in the vicinity of 1% by weight (w/w) of the composition. It will, however, generally be desirable that the water content of many types of embodiments does not exceed about 0.8% w/w, more desirably about 0.6% w/w, and a very desirable upper limit will often be about 0.5% w/w. For certain embodiments, an upper limit for the water content of about 0.2% w/w may be appropriate in order to achieve adequate stability of the composition.

Water content may suitably be determined, for example, by means of so-called Karl Fischer titration [see, e.g., J. S. Fritz and G. H. Schenk, Jr., *Quantitative Analytical Chemistry*, 2nd edition, Allyn and Bacon, Inc., Boston (1969), p. 276, and reference given therein].

Preparation of Compositions of the Invention

With regard to the preparation of a composition according to the invention, a number of approaches are applicable, depending mainly on the form in which the enzyme(s) to be incorporated therein are initially available: If the enzyme(s) is/are available in the form of a substantially water-free solid preparation, the solid enzyme preparation (optionally together with other components of the composition, particularly components which are insoluble, or are at least of low solublility, in the liquid phase employed) may—subsequent to any comminution step which may be necessary to achieve appropriately sized solid particles—simply be dispersed, where appropriate in conjunction with the addition of one or more suitable dispersing agents, in the non-aqueous liquid phase in question by methods known per se.

In cases where the enzyme(s) is/are available as an aqueous solution or concentrate, it is often possible to add to the solution/concentrate a non-aqueous—often water-immiscible—liquid substance (e.g. a paraffin oil or the like) which is inert towards the components of the solution/concentrate and forms an azeotrope with water, and which therefore—under appropriate temperature and pressure conditions—may be used to remove water from the solution/concentrate by distillation (see, e.g., EP 0 696 315). In such cases it may be appropriate to add, portionwise at intervals during the course of the distillation process (and, optionally, at the beginning of the distillation process), another non-aqueous liquid which either alone or in combination with one or more other non-aqueous liquids is is to make up the liquid phase of the final composition of the invention. Alternatively, aqueous enzyme solutions or concentrates may be subjected, e.g., to a spray-drying procedure, whereafter the resulting dried, solid, enzyme preparation may be treated as already described above.

The above-described procedures for the preparation of a composition according to the invention constitute aspects of the present invention.

Enzymes

Enzyme classification numbers (EC numbers) referred to in the present specification with claims are in accordance with the *Recommendations* (1992) *of the Nomenclature Committee of the International Union of Biochemistry and Molecular Biology*, Academic Press Inc., 1992.

Numerous types of enzyme may be incorporated in a substantially water-free, liquid composition of the invention. These include, but are not limited to, the following:

oxidoreductases (EC 1) [including phenol-oxidases such as laccases (EC 1.10.3.2) and other laccase-related enzymes classified under EC 1.10.3; and peroxidases (EC 1.11.1), such as those classified under EC 1.11.1.7];

hydrolases (EC 3) [including proteases (peptidases, EC 3.4); carboxylic ester hydrolases (EC 3.1.1), such as lipases (e.g. triacylglycerol lipases, EC 3.1.1.3) and pectinesterases (EC 3.1.1.11); glycosidases (EC 3.2), such as amylases (e.g. α-amylases, EC 3.2.1.1, and β-amylases, EC 3.2.1.2), cellulases (e.g. endo-1,4-β-glucanases, EC 3.2.1.4) and xylanases (e.g. xylan endo-1,3-β-xylosidases, EC 3.2.1.32)]; and transferases (EC 2) [including aminoacyltransferases (EC 2.3.2), such as protein-glutamine γ-glutamyltransferases (also known as transglutaminases; EC 2.3.2.13)].

Although the enzyme in a composition of the invention may—if the solubility of the enzyme in the non-aqueous liquid phase is sufficiently high—be wholly or partly present in dissolved form, it is generally highly preferable that the enzyme is predominantly or essentially exclusively present in solid (amorphous and/or crystalline), generally particulate, form, preferably dispersed in the liquid phase. Crystalline forms of enzymes are generally very suitable in this connection. The substantial absence of water in compositions according to the invention makes it generally possible to employ free enzymes (i.e. enzymes which are not encapsulated or coated in any manner) in such embodiments.

In some cases it may be appropriate to incorporate two or more different enzymes in a composition of the invention.

Enzymes for which the present invention is particularly useful include oxidoreductases, notably certain oxidases (such as those oxidases classified under EC 1.10.3) and peroxidases (EC 1.11.1).

Oxidases

Preferred oxidases in the context of the present invention are oxidases classified under EC 1.10.3, which are oxidases employing molecular oxygen as acceptor (i.e. enzymes catalyzing oxidation reactions in which molecular oxygen functions as oxidizing agent).

Laccases (EC 1.10.3.2) are very suitable oxidases in the context of the invention. Examples of other useful oxidases in the context of the invention include the catechol oxidases (EC 1.10.3.1).

Laccases are obtainable from a variety of microbial sources, notably bacteria and fungi (including filamentous fungi and yeasts), and suitable examples of laccases are to found among those obtainable from fungi, including laccases obtainable from strains of Aspergillus, Neurospora (e.g. *N. crassa*), Podospora, Botrytis, Collybia, Fomes, Lentinus, Pleurotus, Trametes [some species/strains of which are known by various names and/or have previously been classified within other genera; e.g. *Trametes villosa=T. pinsitus= Polyporus pinsitis* (also known as *P. pinsitus* or *P. villosus*)= *Coriolus pinsitus*], Polyporus, Rhizoctonia (e.g. *R. solani*), Coprinus (e.g. *C. plicatilis*), *P. satyrella*, Myceliophthora (e.g. *M. thermophila*), Schytaldium, Phlebia (e.g. *P. radita*; see WO 92/01046), Coriolus (e.g. C.hirsutus; see JP 2-238885), Pyricularia or Rigidoporus.

Preferred laccases in the context of the invention include laccase obtainable from *Myceliophthora thermophila* and laccase obtainable from *Trametes villosa*.

Also of interest in the context of the invention, particularly in connection with the use of a composition of the invention in the treatment (e.g. bleaching) of cellulose-containing fabric or textile, are modified oxidases, e.g. modified laccases, comprising an N-terminal, C-terminal and/or internal cellulose-binding domain [CBD; see, e.g., P. Tomme et al., *Cellulose-Binding Domains—Classification and ProDerties* in *Enzymatic Degradation of Insoluble Carbohydrates*, John N. Saddler and Michael H. Penner (Eds.), ACS Symposium Series, No. 618 (1996)]. Recombinant techniques suitable for the production of CBD/enzyme hybrids are described, for example, in WO 90/00609, WO 94/24158, WO 95/16782 and by Greenwood et al. in *Biotechnology and Bioengineering* 44 (1994), pp. 1295–1305. They may, for example, be prepared by transforming into a host cell a DNA construct comprising at least a fragment of DNA encoding the cellulose-binding domain ligated, with or without a linker, to a DNA sequence encoding the enzyme of interest (e.g. a laccase) and growing the transformed host cell to express the recombinant product (modified enzyme comprising CBD).

For laccases (as well as modified laccases), the amount of laccase incorporated in a composition of the invention will generally be within the range of 0.0001–500 mg (as pure enzyme protein) per gram of composition, more typically in the range of 0.01–50 mg/g. The level of laccase incorporated in a given composition will depend, inter alia, on whether or not large amounts of substances such as buffers or other pH-regulating substances are to be incorporated in the composition. For a typical composition of the invention containing a laccase, a laccase substrate such as a mediator (vide supra), and a buffer in an amount adequate to maintain a suitable pH in an aqueous medium into which the composition is introduced, the laccase concentration in such a composition will suitably be in the range of about 0.1–5 mg/g, such as in the range of 0.25–2 mg/g (as pure laccase protein), often in the range of 0.5–1 mg/g.

Peroxidases

Peroxidases (EC 1.11.1) are enzymes acting on a peroxide (e.g. hydrogen peroxide) as acceptor. Peroxidase enzymes incorporated in a composition of the invention are very suitably peroxidases obtainable from plants (e.g. horseradish peroxidase or soy bean peroxidase) or from microorganisms, such as fungi or bacteria. In this respect, some preferred fungi include strains belonging to the subdivision Deuteromycotina, class Hyphomycetes, e.g. Fusarium, Humicola, Tricoderma, Myrothecium, Verticilum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes.*

Other preferred fungi include strains belonging to the subdivision Basidiomycotina, class Basidiomycetes, e.g. Coprinus, Phanerochaete, Coriolus or Trametes, in particular *Coprinus cinereus* f. *microsporus* (IFO 8371), *Coprinus macrorhizus, Phanerochaete chrysosporium* (e.g. NA-12) or *Trametes versicolor* (e.g. PR4 28-A).

Further preferred fungi include strains belonging to the subdivision Zygomycotina, class Mycoraceae, e.g. Rhizopus or Mucor, in particular *Mucor hiemalis.*

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium.*

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g. *M. virescens.*

Other potential sources of useful particular peroxidases are listed in B. C. Saunders et al., *Peroxidase*, London 1964, pp. 41–43.

Preferred peroxidases in the context of the invention include peroxidases classified under EC 1.11.1.7. The peroxidase may furthermore be one which is producible by a method comprising cultivating a host cell—transformed with a recombinant DNA vector which carries a DNA sequence encoding said peroxidase as well as DNA sequences encoding functions permitting the expression of the DNA sequence encoding the peroxidase—in a culture medium under conditions permitting the expression of the peroxidase, and recovering the peroxidase from the culture.

A suitable recombinantly produced peroxidase is a peroxidase derived from a Coprinus sp., in particular *C. macrorhizus* or *C. cinereus* according to WO 92/16634.

Also of interest in the context of the invention, particularly in connection with the use of a composition of the invention in the treatment (e.g. bleaching) of cellulose-containing fabric or textile, are modified peroxidases comprising an N-terminal, C-terminal and/or internal cellulose-binding domain (CBD). Such modified peroxidases (CBD/peroxidase hybrids) may be produced by methods referred to above in connection with oxidases.

In the case of peroxidases (as well as modified peroxidases), an amount thereof in the range of 0.02–500 mg (as pure enzyme protein) per gram of composition, such as amount in the range of 0.05–100 mg per gram of composition, will normally be employed. As with laccases (vide supra), the level of peroxidase employed in a particular composition will depend, inter alia, on whether large amounts of other substances (such as a pH-regulating agent) are to be incorporated in the composition.

Enzyme Substrates, Substrate Precursors and Cofactors

Component substances of the type (B) in a substantially water-free liquid composition of the invention (i.e. enzyme substrates, enzyme substrate precursors or enzyme cofactors) may—depending, inter alia, on the solubility of the substance(s) in question in the non-aqueous liquid phase in question—be in dissolved and/or dispersed form in the composition.

Enzyme Substrates

The term "substrate" as employed in the present specification and claims in connection with an enzyme refers to a substance which is a reactant in a reaction catalyzed by the enzyme. When it is appropriate to incorporate an enzyme substrate in a composition of the invention as disclosed herein, the nature of the enzyme substrate(s) suitable for this purpose will depend, inter alia, not only on the type of enzyme (e.g. an oxidoreductase, amylase, lipase, peptidase, etc.) which is to be present in the composition, but also on the intended application of the composition.

Substrates for Oxidoreductases (i) Mediators: Important embodiments of a composition of the invention are compositions comprising an oxidoreductase (e.g. a laccase and/or a peroxidase) together with an oxidizable substrate therefor which functions as a mediator (vide supra). The mediator in a composition of the invention can be any mediator appropriate for use with an oxidoreductase of the type in question (e.g. laccase or peroxidase) employed. Examples of mediators include the following: halide ions (e.g. chloride and bromide); certain metal ions (e.g. $Mn^{2+}$); phenolic species [e.g. acetosyringone (4-hydroxy-3,5-dimethoxyacetophenone), syringaldehyde (4-hydroxy-3,5-dimethoxybenzaldehyde), syringic acid (4-hydroxy-3,5-dimethoxybenzoic acid), alkyl syringates (such as methyl, ethyl, propyl, butyl, hexyl or octyl syringate) and other syringic acid esters [e.g. syringate esters of polyethylene glycols (PEG's) of various molecular weights, such as a PEG 4000 syringate], ethyl 3-(4-hydroxy-3,5-dimethoxyphenyl)acrylate, p-hydroxycinnamic acid, 2,4-dichlorophenol, vanillin, 7-hydroxycoumarin, 6-hydroxy-2-naphthoic acid, and p-hydroxybenzenesulfonate]; 2,2'-azino-bis(3-ethylbenzothiazoline-6-sulfonate) (ABTS; see, e.g., WO 94/12620); and 10-methyl-, 10-ethyl- and 10-propylphenothiazine (see, e.g., WO 94/12621). Other suitable mediators are disclosed in, e.g., WO 94/12619, WO 94/12620 and WO 94/12621.

Mediators of the syringate, phenoxazine or phenothiazine type are generally very suitable in the context of the invention, and some examples hereof are acetosyringone, methyl syringate, 10-phenothiazinepropionic acid, 10-ethylphenothiazine4-arboxylic acid, 10-phenoxazinepropionic acid and 10-methylphenoxazine (described in WO 94/12621).

Mediator will generally be present in a composition of the invention in an amount of from to $10^{-7}$ to $10^{-2}$ mol/g of composition, and often in an amount of from $10^{-5}$ to $10^{-3}$ mol/g of composition.

(ii) Dye precursors: Further important embodiments of a composition of the invention are compositions comprising an oxidoreductase (e.g. a laccase or a peroxidase, often very suitably a laccase, such as one of the laccases mentioned above) together with one or more oxidizable substrates therefor in the form of dye precursor(s) which in the presence of water undergo(es) oxidoreductase-catalyzed oxidation (in general oxidative radical formation) and subsequently polymerize(s) to form a dye of a particular colour. Such oxidoreductase-mediated dye formation has important industrial applications in the dyeing of textiles (e.g. wool, cotton and/or synthetics), yam, fur, hides and the like, and in the field of human personal care, where it has been found to be well suited for use, e.g., in dyeing hair.

As used in the present specification and claims, the term "dye precursor" is intended to embrace not only an individual substance which upon oxidation in the presence of an oxidoreductase gives rise to a strongly coloured dye, but also an individual substance which upon oxidation in a corresponding manner does not itself, alone, give rise to a product having a strong colour, but which when subjected to oxidation in the presence of a substance in the former category of strongly colouring substances leads to a modification of the dye colour which results. Oxidizable substances which exert such a modifying effect on the overall dye colour (such substances sometimes being referred to as "modifiers") are thus included within the meaning of the term "dye precursor" as employed in the context of the invention.

Examples of dye precursors suitable for incorporation in a composition of the invention include, but are not limited to: aromatic diamines; di-amino-substituted aromatic carboxylic acids and esters thereof; aminophenols; phenols; naphthols; and phenolic derivatives of cinnamic acids and esters thereof.

Examples of aromatic diamines include:
2-methyl- 1,4-diaminobenzene,
4-methyl-o-phenylenediamine,
1,4-diamino-benzene (p-phenylenediamine),
2-methoxy-p-phenylenediamine,
2-methyl-1,4-diamino-benzene (p-toluylenediamine),
2-chloro-1,4-diamino-benzene (o-chloro-p-phenylenediamine),
4-amino diphenylamine (N-phenyl-p-phenylenediamine),
1-amino-4-β-methoxyethylamino-benzene (N-β-methoxyethyl p-phenylenediamine),
1-amino-4-bis-(β-hydroxyethyl)-aminobenzene (N,N-bis-(β-hydroxyethyl)-p-phenylenediamine),
1,3-diamino-benzene (m-phenylenediamine),
2-methyl-1,3-diamino-benzene (2,6-diaminotoluene),
2,4-diaminotoluene, and
2,6-diaminopyridine.

Examples of di-amino-substituted aromatic carboxylic acids and esters thereof include:
2,3-diaminobenzoic acid,
3,4-diaminobenzoic acid,
and esters, e.g. lower alkyl esters (such as methyl, ethyl, propyl, 2-propyl or butyl esters), of these Examples of aminophenols include:
1-hydroxy-2-amino-benzene (o-aminophenol),
1-hydroxy-3-amino-benzene (m-aminophenol),
1-methyl-2-hydroxy-4-amino-benzene (3-amino o-cresol),
1-methyl-2-hydroxy4-β-hydroxyethylamino-benzene (2-hydroxy4-β-hydroxyethylamino-toluene),
1-hydroxy-4-amino-benzene (p-aminophenol),
1-hydroxy-4-methylamino-benzene (p-methylaminophenol),
1-methoxy-2,4-diamino-benzene (2,4-diaminoanisole),
1-ethoxy-2,3-diamono-benzene (2,4-diaminophenetole), and
1-β-hydroxyethyloxy-2,4-diamino-benzene (2,4-diaminophenoxyethanol).

Examples of phenols and naphthols include:
1,2-dihydroxybenzene (pyrocatechol),
1,3-dihydroxybenzene (resorcinol),
1,3-dihydroxy-2-methylbenzene (2-methyl resorcinol),
1,3-dihydroxy-4-chlorobenzene (4-chloro resorcinol),
1,2,3-trihydroxybenzene (pyrogallol),
1,2,4-trihydroxybenzene,
1,2,4-trihydroxy-5-methylbenzene (2,4,5-trihydroxytoluene),
1,2,4-trihydroxytoluene,
1,5-dihydroxynaphthalene,
1,4-dihydroxybenzene (hydroquinone), and
1-hydroxynaphthalene (α-naphthol).

Examples of phenolic derivatives of cinnamic acids and esters thereof include:
p-coumaric acid (i.e. 4-hydroxycinnamic acid),
caffeic acid (i.e. 3,4-dihydroxycinnamic acid),
sinapinic acid (sinapic acid; i.e. 3,5dimethoxy-4-hydroxycinnamic acid),
ferulic acid (i.e. 4-hydroxy-3-methoxycinnamic acid),
and esters, e.g. lower alkyl esters (such as methyl, ethyl, propyl, 2-propyl or butyl esters), of any of these.

In the case of cinnamic acid derivatives such as those mentioned above (all of which are commercially available), it does not appear to have been established clearly whether they comprise one or both of the two possible geometric forms (cis and trans, respectively); it appears likely, however, that the trans form is generally predominant.

Other substances of interest as dye precursors in the context of the invention include salicylic acid (i.e. 2-hydroxybenzoic acid) and esters (e.g. lower alkyl esters, such as methyl, ethyl, propyl, 2-propyl or butyl esters) thereof.

(iii) Other substrates for oxidoreductases: Oxidoreductases such as laccases have proved to be very suitable for causing gelling of polysaccharides containing phenolic substituents (e.g. arabinoxylans from wheat or bran, or pectins from sugar beet and related plants) for food applications or for the preparation of highly water-absorbent materials (see, e.g. WO 96/03440). Similarly, laccases and peroxidases have proved to have very useful applications in the preparation of lignocellulose-based products from lignocellulosic material (e.g. wood pulp) and phenolic polysaccharides such as the arabinoxylans or pectins mentioned above (see, e.g., WO 96/03546).

It would thus be appropriate to provide a composition of the invention comprising, for example, suitable levels of a laccase and a laccase substrate in the form of a phenolic polysaccharide. Such a ready-made, storage-stable composition could be employed to advantage for applications as mentioned above.

Substrates for Other Classes of Enzymes

Compositions according to the invention are by no means limited to compositions containing oxidoreductases, and a wide variety of other types of enzymes (e.g. hydrolases such as peptidases, lipases, pectinesterases, glycosidases and cellulases) may be incorporated in compositions according to the invention, together with, e.g., an appropriate enzyme substrate.

By way of example, a pectinesterase may be incorporated in a composition according to the invention together with a substrate therefor in the form of a pectin (e.g. a sugar beet pectin). On bringing the composition into contact with an aqueous medium, hydrolysis of ester linkages in the pectin will occur with subsequent gelling of the resulting, partially hydrolyzed pectin. Gelling in this manner has numerous food and non-food applications (vide infra).

Among further examples of enzyme substrate/enzyme combinations which may suitably be incorporated in a composition according to the invention may be mentioned: (a) one or more lower carboxylic acid alkyl esters (e.g. ethyl butanoate, ethyl 2-methylpropanoate and the like) in combination with an appropriate lipase; and (b) an animal and/or vegetable protein in combination with an appropriate protease (peptidase). Such compositions may be useful as "flavour development" compositions for imparting, e.g., a "cheesy" taste/aroma (in the case of a carboxylic acid esteraipase combination) or a "meaty" taste/aroma (in the case of a protein/protease combination) to foods or food pre-formulations to which they are added.

With respect to substrates for a particular protease (peptidase), it may be mentioned here that numerous other types of enzymes (which are, of course, proteins), including other proteases, will—at least in principle—function as substrates for the protease. However, preferred protease-containing compositions of the invention are compositions in which other enzymes (for example amylases, lipases, cellulases, oxidoreductases or other proteases), if present, are not the sole substrate(s) or potential substrate(s) for the protease in question, but which comprise one or more other, non-enzymatic, proteinaceous substances (e.g. an animal and/or vegetable protein) which function as a substrate for the protease in question.

Enzyme Substrate Precursors

The term "precursor" as employed in the present specification and claims in relation to a substrate for an enzyme incorporated in a liquid composition of the invention denotes a substance or substances which, under conditions prevailing in the use of the composition, generate(s) the enzyme substrate per se.

One important class of substrate precursors in the context of the present invention is hydrogen peroxide precursors, which are useful for in situ generation of hydrogen peroxide for use as substrate for peroxidase enzymes. Some examples of hydrogen peroxide precursors are the following:

perborates (e.g. alkali metal perborates, such as sodium perborates);

percarbonates (e.g. alkali metal percarbonates, such as sodium percarbonate);

organic peroxyacids [e.g. organic di-peracids of the type

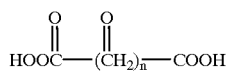

where n is typically an integer below 20, such as diperoxy-dodecanedioic acid (n=10)], and salts thereof (e.g. alkali metal salts, such as sodium salts, thereof); and Systems comprising oxidase enzymes (classified under EC 1) which employ oxygen (e.g. oxygen in the atmosphere) as acceptor and which, in combination with appropriate substrates, generate hydrogen peroxide; such a system may, for example, comprise a monosaccharide oxidase (classified under EC 1.1.3) in combination with the monosaccharide in question [e.g. a glucose oxidase (EC 1.1.3.4) or hexose oxidase (EC 1.1.3.5) in combination with D-glucose, or a galactose oxidase (EC 1.1.3.9) in combination with D-galactose], or an amino acid oxidase (such as one of those classified under EC 1.4.3 or EC 1.5.3) in combination with an appropriate amino acid [e.g. L-lysine oxidase (EC 1.4.3.14) in combination with L-lysine].

Cofactors

The term "cofactor" as employed in the present specification and claims in connection with an enzyme incorporated in a liquid composition of the invention refers to any organic or inorganic factor which is necessary for the activity of the enzyme.

A cofactor is generally a non-protein species of relatively low molecular weight, and may normally be categorized as either (i) a so-called "coenzyme" [e.g. coenzyme A, coenzyme Q (ubiquinone) or coenzyme I (NADP, nicotinamide adenine dinucleotide phosphate)], i.e. a comparatively small organic species whose presence in stiochiometric amounts is essential for the activity of a particular enzyme, or (ii) an inorganic ionic species (e.g. a metal ion, such as $Ca^{2+}$ or $Cu^{2+}$).

An example of a cofactor+enzyme combination appropriate for incorporation in embodiments of a composition of the invention is a calcium salt in combination with a transglutaminase (EC 2.3.2.13). The presence of calcium ($Ca^{2+}$) is important for the activity of certain transglutaminases (which are useful, for example, for cross-linking proteins in meat and meat products), and the ability to "suspend" the activating effect which calcium otherwise will have on such a calcium-dependent transglutaminase by incorporating both components in a composition according to the invention may be of value, for example, for the following reasons:

In the production of transglutaminases on a commercial scale, it is often very difficult to obtain a preparation of the enzyme which is completely free of protease(s). If appropriate measures are not taken, there is then a risk of water-containing preparations of the transglutaminase (which is, of course, a protein) being degraded by such extraneous protease(s), resulting in undesirably rapid loss of transglutaminase activity.

One approach to countering this problem is to add to the preparation a proteinaceous (normally non-enzymatic) substrate upon which the extraneous protease(s) can act and which can thereby "out-compete" the transglutaminase as substrate for the protease(s). This has the drawback, however, that the transglutaminase may (depending on the nature of the proteinaceous substrate in question) cause cross-linking of the proteinaceous substrate, thereby reducing its effectiveness as a substrate for the protease(s) present and, in turn, reducing its protective effect on the transglutaminase.

By formulating a calcium-dependent transglutaminase preparation (possibly containing unwanted protease) and a calcium salt—optionally together with a proteinaceous substrate for protease(s) present—in the form of a substantially anhydrous composition of the invention, it is possible to ensure that the necessary calcium is available, but at the same time avoid the above-mentioned problem of loss of activity of the transglutaminase in the presence of calcium. The possibility of self-catalyzed cross-linking of a calcium-dependent transglutaminase occurring, with attendant loss of enzyme activity, is also substantially eliminated by formulating the transglutaminase and a calcium salt as a composition according to the present invention.

Non-aqueous Liquid Phases

Non-aqueous liquid phases in compositions of the invention may be single components or mixtures of two or more components.

The nature of the non-aqueous liquid phase employed in a composition of the invention will clearly be dependent on, inter alia, the physical and chemical characteristics of the enzyme(s) and the other substances incorporated in the composition, and on the intended use of the final composition. The non-aqueous liquid phase in a composition of the invention may comprise a water-miscible, non-aqueous liquid or a substantially water-immiscible non-aqueous liquid, or both.

Food Applications

When the composition is one intended for direct or indirect use in the preparation of a foodstuff or food ingredient, in particular a foodstuff or food ingredient for human consumption, the non-aqueous liquid phase will normally at least have to meet regulatory and other requirements with regard to safety (lack of toxicity, physiological compatibility, etc.).

For some embodiments of compositions intended for such purposes, the non-aqueous liquid phase may often suitably comprise, for example, one or more edible oils, e.g. soybean oil, corn oil (maize oil) or olive oil, all of which are highly water-immiscible. Other non-aqueous liquid phases of relevance for incorporation in such compositions, optionally—but often very suitably—in combination with one or more edible oils (e.g. one or more of those mentioned above), are certain surface-active agents (surfactants), such as certain non-ionic surfactants of the Spans™ type [e.g. Span™ 20 (sorbitan mono-laurate) or Span™ 80 (sorbitan mono-oleate)] or the Tween™ type [e.g. Tween™ 80 (polyoxyethylene (20) sorbitan mono-oleate), which is readily miscible with water].

Other water-miscible, non-aqueous liquids appropriate for incorporation in some embodiments of compositions of the invention intended for food applications include, for example, hydroxylic liquids such as ethanol, propylene glycol, glycerol, or polyethylene glycols (PEG) of various average molecular weights (e.g. PEG 200, PEG 400 or PEG 600).

Non-food Applications

Non-aqueous liquid phases comprising components selected among those mentioned above are also of relevance in connection with embodiments of a composition of the invention intended for non-food applications. Further water-immiscible, oil-type materials of interest in this connection include, for example, paraffin oils and certain silicone oils. Further surfactants of relevance include liquid, non-ionic surfactants of the ethoxylated and/or propoxylated aliphatic alcohol type [e.g. Softanol™ 50 from BP Chemicals (condensation product of $C_{12}$–$C_{14}$ straight-chain aliphatic alcohol with 5 moles of ethylene oxide)], and of the type represented by Triton™ X-100 (=polyethylene glycol 4-isooctylphenyl ether), i.e. the 1:1 product of etherification-condensation of an alkylphenol (particularly a 4-alkylphenol) with a polyalkylene glycol, substances of this type sometimes being referred to as "alkylphenol alkoxylates".

Further water-miscible, non-aqueous liquid phases appropriate for incorporation in embodiments of a composition of the invention for non-food applications include, for example, ethylene glycol, as well as glycol ethers (such as diethylene glycol dimethyl or diethyl ether).

Other Components

Other components which are appropriate for inclusion in certain embodiments of compositions according to the invention include, but are not limited to, the following:

Dispersing agents: Dispersing agents [i.e. materials which help to prevent or delay separation (e.g. precipitation) of dispersed solid substances] include, e.g.: certain finely divided clays [such as kaolin (china clay), bentonite, fuller's earth and the like]; and naturally occurring and synthetic polymers, e.g. so-called "deflocculating polymers" as well as amphipathic materials of the anionic polymer type.

Viscosity-regulating agents: Examples of materials suitable for increasing the viscosity of embodiments of compositions of the invention include various grades of fumed silica (sold, e.g., under tradenames such as Aerosil™, Cab-O-Sil™ or Tix-O-Sil™), bentonite, kaolin, finely divided calcium carbonate, organo-clays (e.g. Claytone™), and polymeric materials such as hydroxypropylcellulose (e.g. Natrosol™) and xanthan gums.

pH-regulating agents: Examples of pH-regulating agents suitable for incorporation in some embodiments of a composition of the invention [i.e. substances which, when the composition of the invention is brought into contact with an aqueous medium, aid in adjusting and/or maintaining (i.e. buffering) the pH of the medium so as to provide a pH value which is compatible with pH-sensitive components of the composition (such as an enzyme present therein)] include various anhydrous inorganic and organic salts, such as pyrophosphates (e.g. sodium dihydrogen pyrophosphate, $Na_2H_2P_2O_7$), various polyphosphates, potassium dihydrogen phosphate ($KH_2PO_4$), sodium hydrogen carbonate ($NaHCO_3$), potassium acetate ($CH_3COOK$) and sodium acetate ($CH_3COONa$), as well as benzoic acid/benzoate buffers.

Antioxidants: With certain embodiments of compositions of the invention, it may be advantageous to incorporate, in the composition, a substance (an antioxidant) which can protect an oxidation-sensitive component of the composition against oxidation (e.g. by atmospheric oxygen). Such substances include, for example, salts such as sulfites (e.g. sodium sulfite) and thiosulfates (e.g. sodium thiosulfate) as well as organic antioxidants such as methionine, ascorbic acid or lecithins.

Peroxide precursors: As will be apparent from the above discussion in connection with enzyme substrate precursors, in the case of embodiments of compositions of the invention containing, in particular, a peroxidase, it will often be appropriate to incorporate a substance (e.g. an anhydrous perborate, percarbonate, persulfate or the like) which in aqueous medium will provide the requisite hydrogen peroxide.

Detergent composition adjuvants: It will be apparent that certain embodiments of a composition according to the invention (e.g. embodiments comprising a non-aqueous liquid phase in the form of a non-ionic surfactant) can be employed as detergent compositions in their own right. Examples hereof are compositions containing an oxidoreductase, a mediator and a liquid non-ionic surfactant, such compositions being applicable as detergents for washing coloured (dyed) textiles with simultaneous inhibition of dye-transfer.

If appropriate, various adjuvants employed to enhance washing performance of detergent compositions may further be incorporated in such compositions of the invention. Such adjuvants include, but are not limited to the following: further surfactants [e.g. linear alkylbenzenesulfonates (LAS), or alkylpolyglycosides]; soil anti-redeposition agents [e.g. polyvinylpyrrolidone (PVP), or cellulose derivatives such as methylcellulose, hydroxyethylcellulose or carboxymethylcellulose]; and builders (e.g. zeolites, polycarboxylates, phosphates or silicates).

Precursors for disinfective agents: The present invention makes it possible to prepare storage-stable compositions which, when brought into contact with an appropriate aqueous medium, generate an antimicrobial (e.g. fungicidal or bacteriocidal) substance suited for disinfection of a microbially contaminated locus. Such compositions will be useful, e.g., for industrial use as disinfectants for disinfecting microbially contaminated surfaces, areas, objects, utensils and the like, or for personal care use as disinfectants for the disinfection of dentures, contact lenses, skin, wounds, etc. Examples of appropriate formulations of this type are compositions comprising a peroxidase (EC 1.11; such as one of those classified under EC 1.11.1.7), a hydrogen peroxide precursor (e.g. one of those mentioned above in the context of enzyme substrate precursors, such as an alkali metal perborate) and an oxidizable substance [e.g. an iodide ($I^-$) salt such as sodium or potassium iodide] which upon bringing the composition of the invention into contact with an aqueous medium (e.g. water or another aqueous diluent, or a body fluid such as serum or blood) becomes oxidized by the action of the peroxidase/peroxide system and generates a disinfective substance [e.g., in the case of an iodide salt, elemental iodine ($I_2$) and/or triiodide ($I_3^-$)]. In the case of oxidation of iodide to iodine, a peroxidase classified under EC 1.1.1.8 (a so-called "iodide peroxidase" may also be an appropriate peroxidase.

Oligosaccharides: The present inventors have observed, notably in the case of compositions according to the invention comprising a laccase, that the presence of a relatively small amount (e.g. about 1–2% w/w of the composition) of a dextrin (i.e. an oligosaccharide obtainable by partial hydrolysis of starch) can lead to marked enhancement of the storage stability of the composition, particularly at relatively high temperatures (up to about 40° C.). Thus, for example [and as illustrated in the working examples herein (vide infra)], a composition of the invention prepared starting from an alkaline (pH 9) *M. thermophila* laccase concentrate, and containing benzoic acid/sodium benzoate as buffer and ca. 2% w/w of dextrin exhibited remarkable storage stability at 40° C. (measured in terms of retention of bleaching performance); similar results have been observed using, e.g., sodium dihydrogen pyrophosphate as pH-regulating agent instead of benzoic acid/sodium benzoate. In contrast, corresponding compositions containing ca. 2% w/w of maltose or glucose instead of dextrin exhibited significantly poorer storage stability. It thus appears that oligosaccharides such as dextrins can be employed to enhance the stability of certain embodiments of substantially anhydrous liquid compositions of the invention.

Fields of Application of Compositions of the Invention

A number of fields of application have already been mentioned to some extent above. To summarize, non-limiting fields of application of compositions of the invention include, e.g., the following: dyeing of hair; dyeing of textiles; detergent applications (applications in textile washing as a detergent per se, or as an additive for a detergent composition); dye-transfer inhibition in textile washing; bleaching of textiles (e.g. denim bleaching); disinfection; flavour development in foodstuffs; gelling of polysaccharides for use in foodstuffs; and binding of phenolic polysaccharides to lignocellulosic materials (e.g. for preparing fiberboard, paperboard and similar lignocellulose-based materials).

Other interesting applications of the invention in the area of personal care include applications in contact lens cleaning, in dental care and in oral hygiene: Contact lens cleaning/disinfection systems are frequently based on the use of a peroxidase in combination with hydrogen peroxide. Following treatment of contact lenses with such a system, it is important to ensure adequate removal of the cleaning medium, particularly removal of hydrogen peroxide, from the lenses in order to avoid eye irritation or other eye damage. Employing the methodology of the present invention it is, for example, possible to prepare substantially water-free liquid compositions containing a hydrogen peroxide precursor (e.g. one of those already mentioned earlier, above) together with a catalase (EC 1.11.1.6), especially a catalase which has been formulated (e.g. by appropriate coating) as a slow-release or delayed-release product. Using such a composition in combination with a peroxidase for cleaning contact lenses, (a) the requisite hydrogen peroxide for the cleaning/disinfection process will be made available (via reaction of the hydrogen peroxide precursor which takes place in the—normally aqueous—cleaning medium), and (b) remaining hydrogen peroxide will be subsequently destroyed via the action of the catalase which is released into the cleaning medium.

With respect to dental care and oral hygiene applications of the invention, particularly interesting aspects include whitening (bleaching) of teeth and oral disinfection using formulations (e.g. toothpastes, or liquid concentrates which can be diluted in water to give a mouthwash or the like) which constitute substantially water-free compositions of the invention and which, in use, produce hydrogen peroxide. For such purposes, particularly suitable compositions include those containing a hydrogen peroxide generating system comprising a combination of (i) an oxidase enzyme which employs oxygen (e.g. oxygen in the atmosphere) as acceptor and which, in combination with an appropriate substrate, generates hydrogen peroxide, and (ii) a substrate appropriate therefor.

Examples of such systems (some of which have already been mentioned above) include systems comprising:

(a) a monosaccharide oxidase (classified under EC 1.1.3) in combination with the monosaccharide in question [e.g. a glucose oxidase (EC 1.1.3.4) or hexose oxidase (EC 1.1.3.5) in combination with D-glucose, or a galactose oxidase (EC 1.1.3.9) in combination with D-galactose], or (b) an amino acid oxidase (such as one of those classified under EC 1.4.3 or EC 1.5.3) in combination with an appropriate amino acid [e.g. L-lysine oxidase (EC 1.4.3.14) in combination with L-lysine].

A dental care/oral care composition (composition according to the invention) comprising such a hydrogen peroxide generating system may suitably further comprise a peroxidase, e.g. for the purpose of further enhancing the oxidative effect (bleaching/whitening/disinfection effect) which is achieved by the hydrogen peroxide released.

The invention is further illustrated by means of the working examples given below, which are in no way intended to limit the scope of the invention.

Materials and Methods

Materials employed in connection with the working examples given below include the following (supplier and any further details given in parentheses):

*Trametes villosa* laccase (aqueous concentrate produced by Novo Nordisk A/S, Bagsvaerd, Denmark; Mettler dry matter content 29.5% w/w, approximately 20 mg of pure laccase protein per gram of concentrate);

*Myceliophthora thermophila* laccase (aqueous concentrates produced by Novo Nordisk A/S, Bagsvaerd, Denmark; Mettler dry matter content 18.5% w/w or 23.0% w/w; approximately 50 mg of pure, active laccase protein per gram of concentrate);

Isopar™ G (a paraffin oil; Exxon);

Span™ 80 (emulsifier; ICI);

DPX 6592 (an oil-soluble, anionic polymeric, amphipathic dispersing agent; obtained from Allied Colloids Limited, England);

AC31 (an oil-soluble, anionic polymeric, amphipathic dispersing agent; obtained from Allied Colloids Limited, England);

Softanol™ 50 (a non-ionic surfactant of the aliphatic ethoxylated alcohol type, vide supra; BP Chemicals);

glycerol [Food Chemicals Codex (FCC) grade; Solvay or Dow Chemical];

Aerosi™ 200 (fumed silica, specific surface area 200 m$^2$ per gram; Degussa);

Speswhite™ (kaolin; ECC International);

Claycote™ (kaolin; Goonvean);

Glucidex™ D 21 (dextrin; Roquette Freres);

10-phenothiazinepropionic acid (PPT, mediator; Rhone-Poulenc);

methyl syringate (MS, mediator; Inventaa);

o-aminophenol (Aldrich);

m-phenylenediamine (Aldrich);

potassium dihydrogen phosphate ($KH_2PO_4$);

sodium benzoate (powder; Merck);

benzoic acid (powder; Merck);

glycine (Merck);

6" De Meo Virgin Natural White Hair (De Meo Brothers Inc., USA) shampoo (Minirisk™; retail product from SuperBrugsen, Denmark).

EXAMPLE 1

Preparation of a Substantially Anhydrous, PPT-containing Dispersion (Slurry) of Laccase (*T. villosa* laccase)

Preparation of Laccase Dispersion

Per 1000 g of final enzyme dispersion: 263.6 g of Isopar™ G is mixed with 54.0 g of Span™ 80 and 230.0 g of DPX 6592. The mixture is placed in ice. 1017.0 g of *T. villosa* laccase concentrate is added to the cooled mixture within a period of one minute, whilst subjecting the mixture to homogenization (e.g. with a Silverson high shear mixer). Homogenization is continued for 30 minutes so as to obtain an emulsion (aqueous phase in oil phase). During this period the temperature is kept below 15° C. A further 695.4 g of Isopar™ G is then added as diluent.

Water is removed from the resulting emulsion by azeotropic distillation of water/Isopar™ G under vacuum at a constant temperature of about 15° C. After removal of almost all water, 600 g of Softanol™ 50 is added to the de-watered enzyme dispersion. The temperature of the resulting dispersion is then raised to about 90° C. under vacuum in order to remove the remaining Isopar™ G.

The resulting laccase dispersion [30% w/w total solids content; predominant particle size ca. 1.3 µm; water content (as determined by Karl Fischer titration; see, for example, J. S. Fritz and G. H. Schenk, Jr., *Quantitative Analytical Chemistry*. 2nd edition, Allyn and Bacon, Inc., Boston (1969), p. 276 and reference given therein) ca. 0.2% w/w] is cooled to room temperature.

Preparation of PPT-containing Laccase Dispersion (Slurry)

(a) A mixture consisting of 90% w/w of Softanol™ 50 and 10% w/w of Aerosil™ 200 is prepared by adding 0.50 kg of Aerosil™ 200 to 4.50 kg of Softanol™ 50. After stirring, the mixture is homogenised (e.g. on a Fryma mill).

6.0 g of PPT is solubilized in 94 g of the homogenized Softanol™ 50/Aerosil™ 200 mixture with magnetic stirring and heating to ca. 40° C. 94.5 g of the resulting PPT solution is mixed with 5.8 g of the Softanol™ 50/Aerosil™ 200 mixture, 6.3 g of Softanol™ 50, 6.84 g of *T. villosa* laccase dispersion (vide supra) and 75.6 g of $KH_2PO_4$, The mixture is stirred at room temperature and finally homogenized on an Ultra-Turrax apparatus for 2 minutes, giving the final product (ca. 189 g).

(b) A PPT-containing laccase dispersion (slurry) similar to the above, but comprising kaolin as dispersing/thickening agent may be prepared as follows:

A mixture consisting of 89% w/w of Softanol™ 50 and 11% w/w of Aerosil™ 200 is prepared by adding 0.55 kg of Aerosil™ 200 to 4.45 kg of Softanol™ 50. After stirring, the mixture is homogenised (e.g. on a Fryma mill).

54.0 g of PPT is solubilized in 546 g of the homogenized Softanol™ 50/Aerosil™ 200 mixture with magnetic stirring and heating to ca. 40° C. 140 g of the resulting PPT solution is mixed with 63.7 g of the Softanol™ 50/Aerosil™ 200 mixture, 11.5 g of Softanol™ 50, 15.75 g of laccase dispersion, 168 g of $KH_2PO_4$ and 21 g of Speswhite™. The mixture is stirred at room temperature and finally homogenized on an Ultra-Turrax apparatus for 2 minutes, giving the final product (ca. 420 g).

EXAMPLE 2

Use of PPT-containing *T. villosa* Laccase Dispersion (Slurry) for Denim Bleaching (a) Quantification of the Level of Bleaching A Minolta Chroma Meter CR300 was used to quantify the level of bleaching using the change in the colour space (coordinates) L*a*b* (CIELAB system; L* gives the change in black (−L*)/ white (+L*), a* gives the change in green (−a*)/red (+a*), and b* gives the change in blue (−b*)/ yellow (+b*). A decrease in L* means an increase of black colour (decrease of white colour), an increase in L* means an increase in white colour (decrease in black colour), a decrease in a* means an increase in green colour (decrease in red colour), an increase in a* means an increase in red colour (decrease in green colour), a decrease in b* means an increase in blue colour (decrease in yellow colour), and an increase in b* means an increase in yellow colour (decrease in blue colour), in accordance with the table below.

| − (minus) | Coordinate | + (plus) |
|---|---|---|
| Black | L* | White |
| Green | a* | Red |
| Blue | b* | Yellow |

The Minolta Chroma Meter CR300 was operated in the L*a*b* colour space. The light source used was a CIE light standard C. Each measurement was an average of at least 3 measurements. The instrument was calibrated using a Minolta calibration plate (white) with known L*a*b* coordinates (absolute calibration). After calibration on the white plate, the absolute L*a*b* values of the various denim samples (vide infra) were measured several times at different positions on the sample, and the average of the coordinates L*a*b* was calculated. The change in colour of each sample was then calculated as the difference (Δ) between the L*a*b* results for the non-treated and for the treated sample, respectively, i.e. Δ(L*a*b*) was calculated.

(b) Denim Employed

Dakota 14 ounce pure indigo denim (standard fabric from Swift, France) was used. The denim (75×100 cm) was sewn into "legs" (denim cylinders) weighing approximately 350–375 g each (not stone-washed). The denim was washed (125 liter scale wash) in de-ionized water containing Aquazym™ 120 L and Denimax™ T (both available from Novo Nordisk A/S, Bagsvaerd, Denmark) for desizing and abrasion (giving a "stone-washed" appearance) of the denim, respectively, in accordance with the recommendations of the enzyme supplier. No carbonate inactivation was carried out after this washing procedure. After rinsing with 3×125 liters of de-ionized water, the denim was dried in a conventional tumbler dryer, and finally the L*a*b* coordinates were measured as described above.

(c) Bleaching Equipment and Conditions

An Atlas LP2 Launder-o-meter was employed. 2×12 g samples (each measuring ca. 12×22 cm) of the denim treated as described in (b), above, were placed in a tightly sealable stainless steel beaker (total volume 1200 ml) together with 240 ml of de-ionized water (temperature 15–20° C.) and 0.45 g of PPT-containing *T. villosa* laccase dispersion [dispersion containing no kaolin, prepared as in Example 1 (a), or kaolin-containing dispersion prepared as in Example 1 (b), respectively, above]. The beaker was tightly sealed and placed in the Launder-o-meter. The Launder-o-meter was operated at 42 rpm and 60° C. for 30 minutes. Following processing, the pH of the processing liquor in the beaker was measured after cooling, and the denim samples were rinsed in de-ionized water and dried. The L*a*b* coordinates were measured and the extent of bleaching calculated as described above.

(d) Storage Stability (Retention of Denim-bleaching Performance) of PPT-containing *T. villosa* Laccase Dispersions The storage stability of dispersion prepared as in Example 1 (a) (i.e. dispersion containing no kaolin) was examined by incubating samples thereof in the dark at 40° C. and 20° C., respectively, for different periods of time up to 36 days, and then testing the denim-bleaching performance of the various incubated samples using the Launder-o-meter, as described above. The results are shown in the table below, which gives ΔL* values—determined as described above—together with the measured values of the final pH in the cooled processing liquor [cf. section (c), above]:

| Days | 4° C. | | 20° C. | |
|---|---|---|---|---|
| | ΔL* | pH | ΔL* | pH |
| 0 | 7.95 | 6.04 | 7.95 | 6.04 |
| 1 | 10.59 | 6.19 | 10.59 | 6.19 |
| 8 | 9.95 | 6.06 | 10.39 | 6.12 |
| 15 | 10.14 | 5.99 | 9.64 | 6.00 |
| 22 | 10.11 | 5.92 | 10.49 | 5.93 |
| 29 | 10.59 | 6.04 | 9.03 | 6.01 |
| 36 | 10.30 | 6.02 | 9.80 | 6.04 |

In another series of experiments, the storage stability of dispersion prepared as in Example 1 (b) [i.e. dispersion containing kaolin (incorporated as a thickener and/or dispersion stabilizer), which is a presently preferred embodiment of a mediator-containing, laccase dispersion of the type in question] was examined by incubating samples thereof in the dark at 5° C., 25° C. and 40° C., respectively, for different periods of time and then testing the denim-bleaching performance of the various incubated samples using the Launder-o-meter, as described above. The results are shown in the table below, which gives data for periods of time up to 249 days.

| Days | 5° C. | | 25° C. | | 40° C. | |
|---|---|---|---|---|---|---|
| | ΔL* | pH | ΔL* | pH | ΔL* | pH |
| 0 | 11.02 | 6.05 | 11.02 | 6.05 | 11.02 | 6.05 |
| 19 | 10.71 | 5.83 | 10.30 | 5.85 | 10.66 | 5.81 |
| 31 | 10.28 | 5.90 | 11.29 | 5.93 | 9.95 | 5.83 |
| 62 | 8.67 | 5.87 | 9.15 | 5.93 | 5.74 | 5.96 |
| 82 | 10.76 | 5.88 | 10.61 | 5.91 | 5.95 | 5.94 |
| 101 | 10.56 | 5.88 | 9.92 | 6.04 | 5.49 | 6.12 |
| 154 | 10.90 | 6.26 | 11.10 | 6.32 | 5.70 | 6.40 |
| 189 | 10.21 | 5.75 | 8.74 | 5.75 | 3.78 | 6.02 |
| 221 | 10.99 | 5.92 | 8.11 | 5.94 | 3.90 | 6.03 |
| 249 | 10.08 | 5.65 | 9.33 | 5.86 | 3.13 | 6.02 |

It is apparent from the above tables that the dispersions exhibit very good stability at ambient temperatures (about 20–25° C.), and are extremely stable at temperatures of about 5° C. or less. Moreover the data for the kaolin-containing dispersion indicate that satisfactory stability is maintained for a period of at least one month when the dispersion is stored at 40° C.

EXAMPLE 3

Preparation of a Substantially Anhydrous Dispersion of Laccase (*M. thermophila* laccase) Containing Dye Precursor (s) for Hair Colouring (Hair Dyeing)

Preparation of Laccase Dispersion 109.6 g of Isopar™ G is mixed with 9.9 g of Span™ 80 and 42.6 g of DPX 6592. The mixture is placed in ice. 300.4 g of *M. thermophila* laccase concentrate (Mettler dry matter content 18.5% w/w) is added to the cooled mixture within a period of one minute, whilst subjecting the mixture to homogenization (e.g. with a Silverson high shear mixer). Homogenization is continued for 30 minutes so as to obtain an emulsion (aqueous phase in oil phase). During this period the temperature is kept below 15° C. A further 205.2 g of Isopar™ G is then added as diluent.

Water is removed from the resulting emulsion by azeotropic distillation of water/Isopar™ G under vacuum at a constant temperature of about 20° C. After removal of almost all water, 110.8 g of Softanol™ 50 is added to the de-watered enzyme dispersion. The temperature of the resulting dispersion is then raised to about 105° C. under vacuum in order to remove the remaining Isopar™ G.

The resulting laccase dispersion [about 30% w/w total solids content; predominant particle size about 1.6 μm; water content (as determined by standard Karl-Fischer titration, vide supra) ca. 0.55% w/w] is cooled to room temperature.

Preparation of Dye Precursor-containing Laccase Dispersion (Slurry)

(a) A solution of o-aminophenol and m-phenylenediamine in glycerol is prepared by dissolving 0.503 g o-aminophenol and 0.506 g of m-phenylenediamine in 48.02 g of glycerol with magnetic stirring and heating to ca. 40° C. The product is then cooled to room temperature and 1.00 g of *M. thermophila* laccase dispersion (vide supra) is added. The mixture is stirred at room temperature and finally homogenized on an Ultra-Turrax apparatus for 2 minutes, giving the final product [ca. 50 g; containing ca. 1% w/w of o-aminophenol, ca. 1% w/w of m-phenylenediamine and ca. 1 mg of laccase (as pure laccase protein) per gram of final product].

A dye precursor-containing laccase dispersion (slurry) similar to the above, but comprising kaolin as dispersing/thickening agent, may be prepared as follows:

0.517 g of o-aminophenol and 0.499 g of m-phenylenediamine are dissolved in 30.49 g of glycerol with magnetic stirring and heating to ca. 40° C. The product is cooled to room temperature, and 0.95 g of *M. thermophila* laccase dispersion i(vide supra) and 17.44 g of Claycote™ are added. The mixture is stirred at room temperature and finally homogenized on an Ultra-Turrax apparatus for 2 minutes, giving the final product [ca. 50 g; containing ca. 1% w/w of o-aminophenol, ca. 1% w/w of m-phenylenediamine, ca. 35% w/w of kaolin and ca. 1 mg of laccase (as pure laccase protein) per gram of final product].

EXAMPLE 4
Dyeing of Hair Using a Substantially Anhydrous Dispersion of *M. thermophila* Laccase Containing Dye Precursor(s)

Dye precursor-containing laccase dispersions (slurries) prepared as in sections (a) and (b) (dispersions without kaolin and with kaolin, respectively) of Example 3, above, respectively, were used to dye standard test hair ("De Meo Natural Virgin White Hair"), as described in the following:

(i) Hair-dyeing Procedure (a) A tress (1 gram) of the standard test hair was immersed in a freshly prepared dyeing medium produced by mixing 0.5 grams of precursor-containing dispersion and aqueous potassium phosphate buffer, pH 7 (total volume of dyeing medium 5 ml) for 30 minutes at 30° C. The dyed hair sample was then rinsed in running tap water, washed once with shampoo ("Minirisk"), rinsed again in tap water, combed and air-dried.

Using this procedure, one tress was dyed using precursor-containing dispersion without kaolin, whilst a second tress was dyed using precursor-containing dispersion with kaolin.

(b) For comparision purposes (control), a further 1 gram tress of test hair was incubated at 30° C. for 30 minutes in a freshly prepared aqueous medium containing *M. thermophila* laccase (a dilution of the aqueous concentrate referred to above in aqueous potassium phosphate buffer, pH 7) and the same dye precursors as before (solution thereof in aqueous potassium phosphate buffer, pH 7) in the same concentrations as in the dyeing media employed in "(a)", above. The dyed hair tress was then treated in exactly the same manner as in "(a)", above.

(ii) Assessment of Hair Colour

The colour of the dyed hair tresses was assessed quantitatively in a manner similar to that described in Example 2, above, on the basis of measurements of changes ($\Delta$) in the colour parameters $L^*$, $a^*$ and $b^*$, using a Minolta CR200 Chroma Meter.

$\Delta L^*$, $\Delta a^*$ and $\Delta b^*$ are defined relative to the values of $L^*$, $a^*$ and $b^*$, respectively, for the untreated hair (e.g. $\Delta L^* = L^*_{sample} - L^*_{untreated\ hair}$)

The quantity $\Delta E^*$ is then calculated as $\Delta E^* = \sqrt{(\Delta L^{*2} + \Delta a^{*2} + \Delta b^{*2})}$ and is taken as measure of the total quantitative colour change.

FIG. 1 shows the dyeing results ($\Delta L^*$, $\Delta a^*$, $\Delta b^*$ and $\Delta E^*$ values) obtained using 1) the dyeing medium prepared from dispersion according to the invention without kaolin (light grey hatching; middle columns),
2) the dyeing medium prepared from dispersion according to the invention with kaolin (dark grey hatching; right-hand columns) and
3) the control dyeing medium (medium grey hatching; left-hand columns).

It is apparent from the results that the hair-dyeing achieved using compositions according to the present invention (comprising not only enzyme, but also requisite dye precursors) compares very favourably with that achieved using the more "traditional" approach which necessitates "in situ" mixing of enzyme and dye precursor(s), respectively, immediately prior to carrying out the dyeing procedure.

EXAMPLE 5
Preparation of a Substantially Anhydrous, MS-containing Dispersion of Laccase (*M. thermophila* Laccase)

Preparation of Laccase Dispersion 67.1 g of Isopar™ G is mixed with 9.2 g of Span™ 80 and 26.1 g of AC31. The mixture is placed in ice. 200.3 g of a dextrin-containing *M. thermophila* laccase concentrate, pH 9.0 [prepared by adding 10.0 g of 2 M glycine buffer, pH 9.0, and 4.1 g of Glucidex™ D21 to 190.2 g of aqueous laccase concentrate (23.0% w/w Mettler dry matter content)] is added to the cooled mixture within a period of one minute, whilst subjecting the mixture to homogenization (e.g. with a Silverson high shear mixer). Homogenization is continued for 30 minutes so as to obtain an emulsion (aqueous phase in oil phase). During this period the temperature is kept below 15° C. A further 130.0 g of Isopar™ G is then added as diluent.

Water is removed from the resulting emulsion by azeotropic distillation of water/Isopar™ G under vacuum at a constant temperature of about 20° C. After removal of almost all water, 101.9 g of Softanol™ 50 is added to the de-watered enzyme dispersion. The temperature of the resulting dispersion is then raised to about 105° C. under vacuum in order to remove the remaining Isopar™ G. The resulting laccase dispersion (about 30% w/w total solids content) is cooled to room temperature.

Preparation of MS-containing Laccase Dispersion (Slurry)

A mixture consisting of 92% w/w of Softanol™ 50 and 8% w/w of Aerosil™ 200 is prepared by adding 0.40 kg of Aerosil™ 200 to 4.60 kg of Softanol™ 50. After stirring, the mixture is homogenised (e.g. on a Fryma mill).

40.0 g of methylsyringate (MS) is solubilized in 210.0 g of the homogenized Softanol™ 50/Aerosil™ 200 mixture with magnetic stirring and heating to ca. 40° C. 37.8 g of the resulting MS solution is mixed with 15.0 g of benzoic acid, 15.1 g of sodium benzoate, 2.2 g of the Softanol™ 50/Aerosil™ 200 mixture, 3.8 g of kaolin and about 1.1 g of *M. thermophila* laccase dispersion. The mixture is stirred at room temperature and finally homogenized on an Ultra-Turrax apparatus for 2 minutes, giving the final product (ca. 75 g).

EXAMPLE 6
Use of MS-containing *M. Thermophila* Laccase Dispersion (Slurry) for Denim Bleaching Enzymatically "stone-washed" denim was bleached using MS-containing, *M. thermophila* laccase dispersion (prepared according to Example 5, above) stored at 40° C. for various periods of time. The equipment and methodology employed were otherwise as described in Example 2 (vide supra). The results are shown in the table below:

|  | 40° C. | |
| --- | --- | --- |
| Days | $\Delta L^*$ | pH |
| 0 | 7.79 | 4.62 |
| 21 | 7.61 | 4.97 |
| 28 | 7.26 | 4.65 |
| 36 | 8.33 | 4.62 |

As observed for the PPT-containing, *T villosa* laccase dispersion in Example 2, the latter data indicate that satisfactory stability (retention of bleaching performance) of the MS-containing, *M. thermophila* laccase dispersion in question (which contains 2% w/w of dextrin) is maintained for a period of at least one month when the dispersion is stored at 40° C.

We claim:

1. A method of disinfecting a microbially contaminated locus, comprising applying to the microbially contaminated locus an aqueous medium comprising:
   (a) a laccase; and
   (b) an alkyl syringate.

2. The method of claim 1, wherein the laccase is a Myceliophthora laccase.

3. The method of claim 1, wherein the laccase is a Polyporus laccase.

4. The method of claim 1, wherein the alkyl syringate is selected from the group consisting of methyl, ethyl, propyl, butyl, hexyl and octyl syringate.

5. The method of claim 4, wherein the alkyl syringate is methyl syringate.

* * * * *